United States Patent [19]
First

[11] Patent Number: 6,063,768
[45] Date of Patent: *May 16, 2000

[54] APPLICATION OF BOTULINUM TOXIN TO THE MANAGEMENT OF NEUROGENIC INFLAMMATORY DISORDERS

[76] Inventor: Eric R. First, 52-N-St., South Boston, Mass. 02127

[*] Notice: This patent issued on a continued prosecution application filed under 37 CFR 1.53(d), and is subject to the twenty year patent term provisions of 35 U.S.C. 154(a)(2).

[21] Appl. No.: 08/923,884

[22] Filed: Sep. 4, 1997

Related U.S. Application Data

[60] Provisional application No. 60/020,400, Sep. 6, 1996, abandoned.

[51] Int. Cl.⁷ .......................... A61K 38/00; A61K 45/00; A61K 45/05
[52] U.S. Cl. ................................ 514/14; 514/2; 514/825; 514/885; 424/282.1; 424/810; 435/842
[58] Field of Search ................................ 514/2, 14, 825, 514/885; 424/282.1, 810; 435/842

[56] References Cited

U.S. PATENT DOCUMENTS

| | | | |
|---|---|---|---|
| 4,921,757 | 5/1990 | Wheatley et al. | 428/402.2 |
| 5,670,484 | 9/1997 | Binder | 514/14 |
| 5,674,205 | 10/1997 | Pasricha et al. | 604/232 |
| 5,677,274 | 10/1997 | Leppla et al. | 514/2 |
| 5,714,468 | 2/1998 | Binder | 514/14 |

FOREIGN PATENT DOCUMENTS

| | | |
|---|---|---|
| 95/17904 | 7/1995 | WIPO . |
| 95/28171 | 10/1995 | WIPO . |

OTHER PUBLICATIONS

Asada et al. Laser Ther. vol. 3, No. 2, pp. 77–82, 1991.
Caudle et al. Orthopedics. vol. 12, No. 5, pp. 735, 1989.
Lianga et al. J. Rheumotol. vol. 13, No. 1, pp. 230–231, 1986.

*Primary Examiner*—Leon B. Lankford, Jr.
*Assistant Examiner*—Christopher R. Tate
*Attorney, Agent, or Firm*—Thomas J. Engellenner; Nutter, McClennen & Fish LLP

[57] ABSTRACT

The present invention provides a method for the use of at least one serotype or a combination of serotypes of Botulinum neurotoxin either alone or in combination with other peptides or fusion proteins, that when administered in a safe and effective amount, antagonize and therefore decrease or block inflammation induced by the neurogenic mechanisms underlying or associated with inflammatory disorders, in particular, arthritis.

6 Claims, No Drawings

APPLICATION OF BOTULINUM TOXIN TO THE MANAGEMENT OF NEUROGENIC INFLAMMATORY DISORDERS

This application is a continuation-in-part of provisional application Ser. No. 60/020,400, filed Sep. 6, 1996, now abandoned.

BACKGROUND OF THE INVENTION

1. Field of the Invention

The present invention provides a novel methods for treating disorders and diseases which have an underlying or associated neurogenic component, e.g. inflammatory diseases such as arthritis, in order to block or suppress inflammation leading to the unpleasant side effects of neuropathic pain associated with the underlying or associated inflammatory response in these diseases/disorders. The present invention provides a method using *Clostridium botulinum* toxins alone or in combination with other serotypes of botulinum toxin or other related toxins, fugl proteins or neuropeptides, to antagonize the release or enzymati, cleave neuropeptides, neurotransmitters and other mediators from, in particular, sensory afferent or efferent neurons, autonomic efferent nerves or secretory cells. In addition, cells that release neuropeptides and other mediators, activators or promoters of inflammation such as sensory and autonomic neurons and other secretory cells play a role in inflammation. Botulinum toxins block the actions of these mediators by acting enzymatically via the metallopeptidase or related activity associated with the toxins, to cleave peptides critical to normal vesicular secretion and/or proteolytically cleave the peptide mediators

2. Description of Prior Art

Botulinum toxin (BoNT) is a paralytic neurotoxin that has become widely investigated for its therapeutic potential in the treatment of a variety of neuro-muscular disorders including: blepharospasm, spasmodic dysphonia, Strabismus, hemifacial spasm, and adult onset spasmodic torticollis. (Simpson, 1981; Habermann, 1989; Jankovic and Brin, 1991; Borodic et al., 1991; Hambleton, 1992; Schantz and Johnson, 1992; Valtorta and Arslan 1993). Intramuscular injection of nanogram quantities of purified botulinum toxin results in the toxin binding to presynaptic cholinergic nerve terminals and inhibits the release of acetylcholine and thus decreases muscle activity. The result is relaxation of the tonically contracted muscle and thus relaxation of the intended muscle or muscle group.

Botulinum toxin from the Clostridial species is a common term applied, to date to seven immunologically distinct serotypes referred to as A, B, C, D, E, F, and G (Jankovic and Brin, 1990). BoNTs are composed of a heavy chain (MW=100,000Da) and a light chain (MW=50,000Da) joined by disulfide bonds. The light chain is thought to possess a zinc-dependent endopeptidase activity (a metalloendopeptidase) responsible for the cleavage of neuronal proteins. BoNT types A and E cleave the protein SNAP-25, (Blasi et al., 1993a; Binz et al., 1994; Schiavo et al., 1993a,b), BoNT type G cleaves the protein VAMP/synaptobrevin (Yamasaki, 1994). Specifically the B, D, and F toxins cleave VAMP-2/synaptobrevin-2 isoform (Schiavo et al., 1992,1993a,b), and the D and F toxins cleave the VAMP-1/synaptobrevin-1 isoform. BoNT type $C_1$ toxin selectively cleaves HPC-1/syntaxin, in particular, syntaxin 1A and 1B isoforms (Blasi et al., 1993b; Montecucco and Schiavo, 1994; Schiavo et al. 1995). Two laboratories recently reported that BoNT type $C_1$ cleaves not only syntaxin but also has an affinity to cleave the carboxyl terminus of SNAP-25 when studied in chromaffin cells and spinal cord neurons (Foran et al, 1996, Williamson et al., 1996). Proteolytic cleavage of these specific proteins within nerve terminals can result in a profound decrease in normal neurotransmitter release and ultimately the hallmark signs of botulism; diffuse muscular paralysis, impaired vision, and paralysis of the diaphragm leading to suffocation and eventual death. (Donadio et al., 1971; Hughes et al., 1981).

Botulinum toxin is obtained commercially by establishing and growing cultures of C. botulinum in a fermenter and harvesting and purifying the fermented mixture in accordance with known techniques.

Botulinum toxin type A is commercially available for the treatment of the above disorders by Allergan, Inc., Irvine, Calif. under the trade name BOTOX® and from Ipson Boufor, France, under the trade name Dysport®.

The contribution of the nervous system in inflammation has been recognized since Lewis (1932, 1936) proposed that the characteristic wheal and flare responses are mediated by the release of pro-inflammatory substances (described in detail below) from peripheral nerve endings of nociceptive afferent pathways. Fitzgerald (1989) has proposed that an axon reflex mechanism mediates inflammation in the joints. According to the hypothesis the damaged joint transmits neuronal impulses to the spinal cord where, via the axon reflex, signals are transmitted back to nerves at the joint that release pro-inflammatory substances which stimulate or exacerbate inflammation causing further stimulation of C-fibers. In addition postganglionic sympathetic fibers are thought to be stimulated which also release inflammatory substances.

The responses mediated by the peptides and transmitters released from sensory nerves include vasodilatation (via cGRP release), and increased vascular permeability (via SP release) (Jansco et al., 1967; Lembeck and Holzer, 1979; Saria, 1984; McDonald et al., 1996; Anichini et al., 1997; Strittmatter et al., 1997; Carlson et al., 1996; Lundeberg et al., 1996). In addition, the activation of the immune system initiates the attraction of white cells, activation of phagocytic function of neutrophils and macrophages, stimulation of the increased production and release of inflammatory mediators from these cells and the degranulation of mast cells and local release of histamine. (Helme and Andrews, 1979; Siato et al., 1986; Payan et al., 1984; Bar-Shavitz et al., 1980; Hartung et al., 1986; Johnson and Erdos, 1973; Naukkarinen et al., 1996). Substance P has been shown to stimulate the release of prostaglandin E2 and collagenase from cells in joints of patients with rheumatoid arthritis (Lotz et al., 1987), and further, induce the release of immune-active agents such as interleukin 1, tumor necrosis factor and interleukin 6 (Carleson et al., 1996). The result of this neuroendocrine cascade of events has been termed, neurogenic inflammation (Jancso, 1967) and works as a central network modulating the events between the immune, nervous and endocrine systems. A neurogenic disorder involves the release of neuropeptides, neuromodulators and other mediators of the neurogenic response including mediators from the immune nervous and endocrine systems.

There is significant and rapidly growing literature indicating that there is an important neurogenic component of inflammatory diseases, the prototypical example is rheumatoid arthritis (RA) (Heller et al., 1995; Anichini et al., 1997). Both autonomic and sensory afferent nerves have been implicated in the complex mechanisms involved in acute and chronic inflammation associated with RA (Levine et al., 1985; Jessel, 1985, Heller et al., 1995). Two neuropeptides, implicated as mediators of neurogenic inflammation, are Substance P (SP) and calcitonin gene related peptide (cGRP) (Anichini et al., 1997). Recent evidence obtained in a rat model for arthritis indicates that there is an increase in tissue content of the neuropeptides following adjuvant stimulation of joint inflammation in the rat (Ahmed et al., 1995). Additional studies support the role of SP and cGRP in mediating inflammation, leading to neuropathic pain, in which, levels of both are elavated when inflammation is induced (Anichini et al., 1997; Strittmatter et al., 1997; Carlson et al., 1996; Lundeberg et al., 1996). Also very recently pituitary adenylate cyclase-activating peptide (PACAP) has been added to this collection of peptide mediators of neurogenic inflammation and release from sensory nerves (C-fibres) (Wang et al., 1996)

The results of experiments performed in rat models for acute joint inflammation have demonstrated that local joint inflammation stimulated by articular administration of carrageenan is blocked by neurokinin (NK) receptor antagonists (the receptor responsible for binding SP) and the sensory neuron lesioning drug, capsaicin (Lam and Ferrel, 1989, Pierce et al., 1996). Capsaicin is currently used as a therapeutic treatment of inflammation but irritation and application as a topical agent limit the effectiveness. These observations are consistent with earlier observations implicating both of these peptides (SP and cGRP) in arthritis.

Both sensory and sympathetic nerves densely innervate the synovium and these neurons are known to release the neuropeptides SP and cGRP. The levels of the sensory neuropeptides SP and cGRP have been shown to be elevated in the synovium of RA patients. Although recent emphasis has been placed on these two peptides (SP+cGRP), there are a number of other pro-inflammatory mediators that may be involved in neurogenic inflammation such as but not limited to; PACAP, VIP, NK1, 5-HT, TNF, IL-1, IL-6, ACh, nitric oxide (NO), NGF and arachadonic acid.

In addition to the sensory afferent involvement in arthritis, there is also evidence that autonomic efferent input plays a role in acute inflammation and inflammatory disease (Heller et al. 1995; Janig, et al., 1997). Of particular interest are the results of experiments using experimental arthritis in the rat in which sympathetic denervation prevented the development of arthritis (Levine et al., 1986). Interestingly, rheumatoid arthritis patients without particular neurologic complaints showed a high proportion of neurophysiologic abnormalities, indicating the involvement of the sympathetic nervous system (Good et al., 1965).

Botulinum toxin has been shown to inhibit the release of all neurotransmitters and some peptides from efferent motor and autonomic nerves studied to date. It is very likely that the toxin can inhibit all substances that are released from cells by a vesicular mechanism when enough toxin is administered to enter these cells and antagonize vesicular release. This may also be accomplished by methods that temporarily increase the permeability of cells or by packaging the toxin in a form that more readily passes the membrane barrier. One example would be the use of lipid vesicles that would fuse to the membrane of the target cells and allow the toxins contained in these vesicles to enter the cells. As discussed above there is overwhelming evidence that the botulinum toxins inhibit neurotransmitter release by interfering with normal vesicular release mechanisms. Evidence exists that BoNTs do indeed inhibit the release of neuropeptides as evidenced by the data for inhibition of SP (Ashton and Dolly, 1988). Both SP and cGRP are both released from afferent sensory neurons that carry sensory information back to the central nervous system.

The properties of the metalloendopeptidase activity of the light chain of botulinum neurotoxins have been described above. A similar zinc-dependent metalloendopeptidase, neutral endopeptidase is responsible for the degradation of inflammatory mediators such as SP and CGRP (Nadel, 1994; Katayama et al., 1991; Nadel and Borson, 1991). Therefore, it is hypothesized by the inventor that BoNT acts enzymatically to cleave either proteins such as SNAP-25, syntaxin, and synaptobrevin, which are critical to vesicular release or direct cleavage of inflammatory mediators including but not limited to SP, CGRP, PACAP, VIP. The latter cleavage occurs within the cell or neuron and/or after this mediator is released into the extracellular environment. The long-term effects of the toxin are most likely related to the intracellular effects of the proteolytic activity of the toxin.

Arthritis for example, affects approximately 40 million Americans (1 in 7) and with the graying of America it is anticipated that this number will grow from 40 to 60 million by the year 2020. Of the 40 million about two thirds have moderate disease and about 10% are severely affected. Arthritis is the number one cause of disability in America and the estimated annual cost of arthritis is 55 billion dollars in medical care and indirect costs such as lost wages. There are more than 127 different types of arthritis as defined by the Arthritis Foundation. The etiology of arthritis is unknown however, the disease is characterized by chronic inflammation of the synovial joints. Over the last decade it has become increasingly more evident that arthritis, in particular, rheumatoid arthritis (RA) has a neurogenic component. In particular, the nervous system plays an important role in determining the pattern and severity of joint destruction therefore, the nervous system plays a crucial role in the pathophysiology of this chronic disease.

Synovitis has been referred to as the "first and truest kind of arthritis" with RA the prototypical example of this condition. This chronic inflammatory disease can, over many years, result in damage to the joint itself. There are other forms of arthritis that do not involve synovitis yet are characterized by inflammation such as ankylosing spondylitis, which is a genetic disorder and 7% of the US population has the gene (HLA-B27) and therefore, the potential to develop this disease. An estimate of 1% of the population suffers from this disease. Psoriatic arthritis is related to both synovitis and ankylosing spondylitis and can be distinguished by the joints that are affected including the general lack of symmetry of psoriatic joint involvement and the less prominent fatigue, tiredness and stiffness characteristic of rheumatoid arthritis.

In addition to arthritis, it has been proposed that neurogenic inflammation plays a fundamentally important role in the pathophysiology of migraine (Moskowitz, 1993). Working in much the same fashion as in arthritis, candidate mediators of migraine include vasoactive intestinal peptide (VIP), Substance P (SP) and calcitonin gene-related peptide (cGRP) (Goadsby et al., 1988, 1990; Goadsby and MacDonald, 1985; Goadsby and Shelley, 1990; Olesen 1991, 1994.) Another example whereby neurogenic inflammation takes place is in airway diseases, such as asthma, in which inflammatory mediators such as cGRP and SP play a major role in the inflammatory process (Barnes, 1996; Spina, 1996; Fisher et al., 1996).

SUMMARY OF THE INVENTION

The object of the present invention is to utilize botulinum toxins either as individual serotypes or combinations of serotypes that are administered alone or in combination with other compounds, related toxins, or neuropeptide antagonists, for novel treatments of neurogenic disorders that have an underlying or associated neurogenic component, including inflammatory components or noninflammatory components. The mechanism by which this is achieved is through the antagonism of these neuropeptides, neuromediators or other mediators of te neurogenic response, by antagonizing release from sensory afferent and efferent nerves and autonomic afferent nerves or other secretory cells (secretory cells are any cells that release substances and mediate, activate or promote inflammation). In this way BoNTs can specifically, interrupt the pathway of neurogenic disorder resulting in relief of neuropathic pain by treating the disorder.

The present invention provides a method of treating or inhibiting diseases or syndromes with an underlying or associated neurogenic component (neurogenic disorder) by way of antagonizing the actions of neurogenic mediators involved in the disorder. This therapy is accomplished by the use of Clostridium botulinum toxin, combinations of different serotypes of botulinum toxin, and combinations with other toxins, substances such as capsaicin, certain neuropeptide antagonists, or other antagonists of inflammation. Clinically, attention has been focused exclusively on the inhibition of ACh release by botulinum toxins (BoNTs), from peripheral and autonomic efferent nerves, with regard to the importance of this action to the therapeutic management of involuntary movement disorders of which the toxin was originally approved for. However, recent experiments performed under this invention, reveal that the toxin can antagonize the development of inflammation in a classical model of evoked inflammation in the rat paw. Cells which release neuropeptides and other mediators, activators or promoters of inflammation such as sensory and autonomic neurons and other secretory cells may play a crucial role in inflammation. This invention provides for Botulinum toxins to block the actions of these mediators by acting enzymatically via the metallopeptidase or related activity associated with the toxins, to cleave peptides critical to normal vesicular secretion and/or proteolytically cleave the peptide mediators. The present invention provides that BoNTs antagonize the release or enzymatically cleave neuropeptides, neurotransmitters and other mediators release from, but not limited to, sensory afferent or efferent neurons, autonomic efferent nerves and/or secretory cells.

DETAILED DESCRIPTION

Botulinum toxin from the Clostridial species is a common term applied, to the seven immunologically distinct serotypes referred to as A, B, C, D, E, F, and G (Jankovic and Brin, 1990). BoNTs are composed of a heavy chain (MW=100,000Da) and a light chain (MW=50,000Da) joined by disulfide bonds. The light chain possesses zinc-dependent endopeptidase activity that is responsible for the cleavage of neuronal proteins critical to neurotransmitter release. This invention includes the unique proposal this endopeptidase and/or related peptidase activities possessed by the toxin also cleaves peptide mediators of neurogenic inflammation and/or inhibit the release of these mediators by cleavage of proteins (eg. SNAP-25, syntaxin, synaptobrevin) critical to normal neurotransmifter release.

The present invention provides a safe and effective method for the treatment of the following non-limiting examples of diseases that have a neurogenic component to an inflammatory/non-inflammatory response with the above type of compounds or in combination with other related toxins, fusion proteins, and neuropeptides:

Inflammatory Types of Arthritis
Rheumatiod Arthritis
Tenosynovitis (calcific (BCP) other)
Seronegative polyarthritis
Systemic lupus erythemotosus
Mixed connective tissue disease
Ployarteritis
Dermatomyositis
Rheumatic fever
Reiter's syndrome ("reactive" Arthritis)
Psoriatic arthritis
Ankylosing spondylitis
Juvenile rheumatoid arthritis
Inflammatory bowel disease
Crystal synovitis
   Gout
   Pseudogout
   Other; postcorticosteroid injection flare
Polymyalgia rheumatica
Palindromic rheumatism
Viral Arthritis (rubella, mumps, hepatitis B)
Infectious arthritis
   Bacterial
   Tuberculosis
   Fungal
Immune complex Arthritis
   (cryoglobulinemia, bacterial endocarditis, infected ventriculolateral shunt)
Non-inflammatory types of arthritis with a possible neurogenic component
Erosive osteoarthritis
Primary generalized osteoarthritis (OA)
Isolated OA (hip, knee, first CMC)
Cervical syndrome
Traumatic arthritis
Neuroarthropathy (Charcot)
Enthesopathy
Tumors
   pigmented villonodular
   synovitis
   synovial cell sarcoma
Mechanical abnormalities
   (e.g. torn menisci, tibial torsion)
Reflex sympathetic dystrophies
   (e.g. shoulder-hand)
Periarthritis of shoulder
Tendonitis
Carpal tunnel syndrome
Bursitis
Other Diseases
Tumors
Inflammatory bowel disease
Peripheral neuropathy
migraine
asthma The present invention includes the use of Botulinum toxin, either as one serotype or as a combination of serotypes, either alone or in combination with compounds or fusion proteins which inhibit neuro-pathways such as in surgery or trauma, where inflammation develops rapidly and the said compound or combination may inhibit or slow down the inflammatory process related to the injury or surgery.

The present invention alleviates the unpleasant side effect of neuropathic pain that is due to the release of certain neuroinflammatory peptides and other mediators of inflammation, in response to injury/inflammation or disease.

The present invention provides the therapeutic effect of BoNTs involve but not be limited to inhibition of the release of sensory afferent/efferent or autonomic efferent and secretory cell derived mediators of inflammation, (e.g. SP, cGRP, 5-HT, VIP, IL-1, IL-2, TNF, NO, NGF and other cytokines and tachykinins) having a longer lasting therapeutic effect (on the order of weeks or months versus current therapies with a duration of action lasting only hours to days.

The present invention utilizes doses that are effective in the therapeutic treatment of different types of neurogenic inflammatory and non-inflammatory diseases, along with the use in the treatment of trauma/surgery where inflammation is not uncommonly responsible for considerable complications and pain. These diseases and disorders along with trauma and surgical procedures exemplified above, may be treated using a known safe and effective dose range that would be applicable for the disease/disorder or trauma or surgery being treated, since they all appear to have an underlying neurogenic component that may be inhibited. The potency of the toxin is expressed as a multiple of the LD50 value for the mouse, one unit (U) of toxin is defined as the dose sufficient enough to kill 50% of a group of mice, 18–20 gram Swiss Webster mice. Dosage of the toxin is dependent on the area or condition that is to be treated. This could be as high as 1000 U but a more useful range of 5–500 LD50s of botulinum neurotoxin alone or in combination with other toxins, fusion proteins, peptides, or in combination with other compounds such as capsaicin, may be more suitable. However higher or lower doses may be necessary.

The present invention includes methods of administration to treat the above diseases wherein a formulation of botulinum toxin comprising a safe and effective amount of the toxin as outlined above, is injected subcutaneously or intramuscularly, in single or multiple point injections, at or near the site of inflammation, including a joint or joints such as to enter the synovial fluid, using the same technique for needle placement as that used for steroidal treatment of arthritic diseases.

The present invention includes methods upon which the above safe and effective amount of toxin or in combination of stated compounds, is administered by transdermal application to the skin such that the toxin or combination of stated compounds is absorbed through the skin. A safe and effective dose of toxin or combination of stated compounds is contained in a "depot" formulation, that is implanted within or under the appropriate tissue such that controlled release of toxin can be provided over either extended, continuous and/or released in a pulsitile pattern, over certain periods of time. In addition, an aerosolized preparation of botulinum toxin alone or in combination with other serotypes or compounds could be used to treat neurogenic bronchial disorders such as asthma.

The following example illustrates the present invention and is not intended to limit the same.

EXAMPLE 1

In order to validate the hypothesis that BoNT's have the potential therapeutic properties to block inflammatory cascade pathways, experiments were undertaken using a classical model for inflammation. The rat foot paw model of inflammation was utilized in which carrageenan is employed to evoke the inflammatory response following subcutaneous administration. The results of these experiments showed that BONT produced significant antagonism of the profound carrageenan-evoked inflammation.

Methods/Materials

Type A lyophilized *Clostridium botulinum* toxin type A (BOTOX®) produced by Allergan, Inc., Irvine, Calif. was obtained for the experiment (lot #CGB 001, Exp. Date; Feb 98).

A total of 11 white male Wistar rats (150–200 g) where 10 were pretreated by injection into the left ankle (test side) of 50 μl of 30 LD50 units of Hall Strain *Clostridium botulinum* toxin Type A, resuspended in sterile 0.9% saline solution. The number 11 rat was administered the same above dose but was injected I.P., in order to assess the potency of the toxin. Observations after 24 hours confirmed the potency and also, the left ankle showed hallmark signs of paralysis. The right ankle of each of the 10 pretreated rats were injected with sterile saline alone and used as the control side. Upon paralysis, the 10 animals were challenged with 50 μl of 0.1% carrageenan solution, injected into the left and right footpads. Carrageenan is a compound that initiates extreme inflammation almost immediately upon injection. The results of published data show that this response has a significant neurogenic component. Readings were performed by a standardized volumetric fluid displacement analysis which measures the degree of inflammation compared to baseline; taken at baseline, one and three hours.

Results

Statistical analysis was performed using Sigma Stat (Jandell Scientific) software. Data was confirmed statistically and passed the test for normalization of data and therefore a paired t-test was calculated for the 1 and 3 hour readings, with n=10. At 1 hour the data was not significant, with a p-value of 0.38, however, at 3 hours, the data revealed an unexpected 30% reduction in inflammation with a p-value of <0.001. These data confirm that BoNT have an effect on blocking the inflammation mediated by the above mentioned neuropeptides, in particular but not limited to, substance P (SP), and calcitonin related gene product (cGRP), via but not limited to, sensory and efferent nerve pathways; an antidromic response.

Discussion

The rat foot paw model for inflammation is a general model used to screen anti-inflammatory compounds. Thus, this provides a good test of the basic hypothesis that BoNTs can antagonize inflammation. This also provides a challenging test as carrageenan-evoked inflammation involves profound stimulation of inflammation not just involving the proposed mechanisms antagonized by BoNTs. The fact that BoNT produced significant antagonism of this extreme inflammatory response argues strongly for the hypothesis embodied in this invention. In the normal course of neurogenic inflammatory disease such as rheumatoid arthritis, the onset of inflammation is more gradual and therefore antagonism of inflammation by BoNT would be expected to be greater, particularly in the case of rheumatoid arthritis.

REFERENCES

Ahmed, M., Bjurholm, A., Schultzberg, M., Theodorsson, E., and Kreicbergs, A. Increased levels of substance P and calcitonin gene-related peptide in rat adjuvant arthritis. *Arthritis and Rheumatism* 38:699–709, 1995.

Anichini, M., Cesaretti, S., Lepori, M., Maddali Bongi, S., Maresca, M., and Zoppi, M. Substance P in the serum of patients with rheumatoid arthritis. *Revue Du Rhumatism, English edition.* 64 (1): 18–21. 1997.

Ashton, A. C. and Dolly, J. O. Characterization of the inhibitory action of botulinum neurotoxin type A on the release of several transmitters from rat cerebrocortical synaptosomes. *J Neurochem.* 50, 1808–1816, 1988.

Barnes, P. J. Neuroeffector mechanisms: the interface between inflammation and neuronal responses. *J. Allergy Clin. Imm.* 98 (5 pt 2): S73–81, 1996.

Bar-Shavitz, Z., Goldman, R., Stabinsky, Y. et al. Enhancements of phargocytosis—a newly found activity of substance P residing in it N-terminal tetrapeptide. *Biochem Biophys Res. Commun* 94:1445–1451, 1980.

Borodic, G. E., Pearce, L. B., Johnson, E. A. and Schantz, E. J.: Clinical and Scientific Aspects of Botulinum A Toxin. *Ophthalmology Clinics of North America*. 4: 491–504, 1991.

Carleson, J., Alsterfren, P., Appelgren, A., Appelgren, B., Kopp, S., Srinivasan, G. R., Theodorrson, E., and Lundeberg, T. Effects of adjuvant on neuropeptide-like immunoreactivity in experimentally induced temporomandibular arthritis in rats. *Arch. Oral Biol*. 41 (7): 705–12. 1996.

Dray, A. Mechanism of action of capcaisin-like molecules on sensory neurons. *Life Sci*. 51:1759–1765, 1992.

Fisher, A., McGregor, G. P., Sria, A., Philippin, B., and Kummer, W. Induction of tachykinin gene and peptide expression in guinea pig nodose primary afferent neurons by allergic airway inflammation. *J. Clin. Invest*. 98 (10): 2284–91, 1996.

Goadsby, P. J. and Shelley, S. High-frequency stimulation of the facial nerve results in local cortical release of vasoactive intestinal polypeptide in the anesthetized cat. *Neurosci. Leit*. 112:282–289, 1990.

Goadsby, P. J. and Macdonald, G. J. Extracranial vasodilation mediated by vasoactive intestinal polypeptide (VIP). *Br. Res*. 329:285–288, 1985.

Goadsby, P. J., Edvinsson, L., and Ekman, R. Release of vasoactive peptides in the extracerebral circulation of humans and the cat during activation of the trigeminovascular system. *Ann Neurol*. 23:193–196, 1988.

Goadsby, P. J., Edvinsson, L., and Ekman, R. Vasoactive peptide release in the extracerebral circulation of humans during migraine headache. *Ann. Neurol*. 28:183–187, 1990.

Hambleton, P.: *Clostridium Botulinum* Toxins: A General Review of Involvement in Disease, Structure, Mode of Action and Preparation for Clinical Use. *J. Neurol*. 239:16–20,1992.

Hartung, A. R., and Erdos, E. G. Release of histamine from mast cells by vasoactive peptides. *Proc. Soc. Exp. Biol. Med*. 142:1252–1256, 1973.

Heller, P. H., Green, P. G., Tanner, K. D., Miao, F. J-P., and Levine, J. D. Peripheral neural contributions to inflammation. In *Orofacial Pain Tempromandibuar Diseases*, Fricton, J. R., and Dubner, R., Eds., Raven Press, Ltd., New York, chap. 6, 1995.

Helme, R. D., and Andrews, P. V. The effect of nerve lesions on the inflammatory response to injury. *J. Neurosci. Res*. 13:453–459, 1979.

Janig, W., Levine, J. D., and Michalis, M. Interactions of sympathetic and primary afferent neurons following nerve injury and tissue trauma. *Prog. Brain Res*. 113:161–84, 1996.

Nadel, J. A. Modulation of neurogenic inflammation by peptidases. In *neuropeptides in Respiratory Medicine*, Kaliner, M. A., Barnes, P. J., Kunkel, G. H. H., and Baraniuk, J. N., Eds., Marcel Dekker, New York, pg. 351, 1994.

Nadel, J. A., and Borson, D. B. Modulation of neurogenic inflammation by neutral endopeptidase. *Amer. Rev. Respir. Dis*., 143, S33, 1991.

Jankovic, J. and Brin, M.: Therapeutic Uses of Botulinum Toxin. *N. Engl. J. Med*. 324: 1186–1194, 1990.

Jansco, N., Jansco-Gabor, A., and Szoeanyi, J. Direct evidence for direct neurogenic inflammation and its prevention by denervation and pretreatment with capsaicin. *Br. J. Pharmacol. Chemother*. 31: 138–151, 1967.

Jessel, T. M. Cellular interactions at the central and peripheral terminals of primary sensory neurons. *J. Immunology* 135(2): 746s–749s, 1985.

Johnson, A. R., and Erdos, E. G. Release of histamine from mast cells by vasoactive peptides. *Proc. Soc. Exp. Biol. Med*. 142: 1252–1256, 1973.

Katayama, M., Nadel, J. A., Bunnett, N. W., Di Maria, G. U., Haxhiu, M., and Borson, D. B. Catabolism of calcitonin gene-related peptide and substance P by neutral endopeptidase. *Peptides*, 12, 563, 1991.

Leeman, S. E., Gamse, R. Substance P in sensory neurons. *Trends Pharmacol. Sci*. 2:119–121, 1981.

Lembeck, F., and Holzer P. Substance P as a neurogenic mediator of antidromic vasodilation neurogenic plasma extravasation. *Naunyn-Schmiedebergs Arch. Pharmacol*. 310:75–183, 1979.

Levine, J. D., Goetzl, E. J., Basbaum, A. I. Contribution of the nervous system to the pathophysiology of rheumatoid arthritis and other polioarthrides. *Rheum. Dis. Clin. North. Am*. 2: 369–383. 1987.

Lotz, M., Carson, D., Vaughn, J. H. Substance P activation of rheumatoid synoviocytes: Neural pathway in pathogenesis of arthritis. *Science* 241: 1218–1221, 1987.

Lotz, M., Carson, D., Vaughn, J. H. The effect of neuropeptides on production of inflammatory cytokines by human monocytes. *Science* 241: 1218–1221, 1987.

Levine, J. D., Colier, D. H., Basbaum, A. I., Moskowitz, M. A., and Helms, C. A. Hypothesis: The nervous system may contribute to the pathophysiology of rheumatoid arthritis. *J. Rhuematology* 12(3):406–411, 1985.

Levine, J. D., Moskowitz, M. A., and Basbaum, A. I. The contribution of neurogenic inflammation in experimental arthritis. J Immunol. 135: 943s-947s, 1985

Levine, J. D., Dardick, S. J., Roizen, M. F., Heins, C., and Basbaum, A. I. The contributions of sensory afferents and sympathetic efferents to joint injury in experimental arthritis. *J. Neurosci*. 6:3923–3929, 1986.

McDonald, D. M., Bowden, J. J., Baluk, P., and Bunnett, N. W. Neurogenic Inflammation. A model for studying efferent actions of sensory nerves. *Adv. Exp. Med and Biol*. 410: 453–62, 1996.

Moskowitz, M. A. Neurogenic inflammation in the pathophysiology and treatment of migraine. *Neurology* 43(suppl 3): S16–S20, 1993.

Naukkarinen, A., Jarvikallio, A., Lakkalorpi, J., Harvima, I. T., Harvima R. J., and Horsmanheimo, M. Quantitative histochemical analysis of mast cells and sensory nerves in psoriatic skin. *J. Pathol*. 180 (2): 200–5. 1996.

Olesen, J. The clinical and pathophysiological observations in migraine and tension-type headache explained by integration of vascular, supraspinal and myofascial inputs. *Pain* 46: 125–132, 1991.

Olesen, J. Understanding the biologic basis of migraine. *The New Engl. J. Med*. 331:1713–1714, 1994.

Payan, D. G., Levine, J. D., Goetzl, E. J. Modulation of immunity and hypersensitivity sensory neuro-peptides. *J. Immunol*. 132: 1601–1604, 1984.

Pierce, P. A., Xie, G. X., Peroutka, S. J., Levine, J. D. Dual effect of the serotonin agonist, sumatriptan, on peripheral neurognic inflammation. *Regional Aneth*. 21(3): 219–25, 1996.

Saria, A. Substance P in sensory nerve fibers contributes to the development of edema in the rat hind paw after thermal injury. *Br. J. Pharmacol*. 323: 341–342, 1984.

Schantz, E. J. and Johnson, E. A.: Properties and Use of Botulinum Toxin and Other Microbiological Neurotoxins in Medicine. *Microbiol Rev*. 50(1): 80–99, 1992.

Siato, A., Kimura, S., Goto, K. Calcitonin gene-related peptide as potential neurotransmitter in guinea pig right atrium. *Am. J. Physiol.* 250: H693–H698, 1986.

Sluka, K. A. Pain mechanisms involved in musculoskeletal disorders. *J. Orth. Sports Physical Ther.* 24 (4): 240–54.

Spina, D. Airway sensory nerves: a burning issue in asthma? Thorax 51 (3): 335–7, 1996.

Strittmatter, M., Grauer, M., Isenberg, E., Hamann, G., Fischer, C., Hoffmann, K. H., Blaes, F., and Schimrigk, K. Cerebrospinal fluid neuropeptides and monoaminergic transmitters in patients with trigeminal neuralgia. *Headache* 37(4): 211–6. 1997.

Wang ZY. Waldeck K. Grundemar L. Hakanson R. Ocular inflammation induced by electroconvulsive treatment: contribution of nitric oxide and neuropeptides mobilized from C-fibres. *Br. J Pharm.* 120 (8):1491–6, 1997.

I claim:

1. A method for treating neurogenic inflammation comprising, administering a therapeutically effective amount of *Clostridium botulinum* toxin to antagonize the action of at least one neurogenic inflammatory mediator, whereby said toxin interrupts a neurogenic pathway associated with said neurogenic inflammation.

2. The method of claim 1, wherein the botulinum toxin is selected from the group consisting of botulinum toxin A, B, C, D, E, F and G.

3. The method of claim 1, further comprising treating the neurogenic inflammation by inhibiting at least one neurogenic inflammatory mediator selected from the group consisting of substance-P (SP), calcitonin gene-related peptide (cGRP), vasoactive intestinal peptide (VIP), interleukin-1 (IL-1), interleukin-2 (IL-2), nitric oxide (NO), 5-hydroxytryptamine (5-HT), tumor necrosis factor (TNF), and nerve growth factor (NGF).

4. The method of claim 1, wherein the botulinum toxin is less than about, or equal to 1000 U.

5. The method of claim 1, wherein the neurogenic inflammation is caused by rheumatoid arthritis.

6. The method of claim 1, wherein the neurogenic inflammation is caused by gout.

* * * * *

UNITED STATES PATENT AND TRADEMARK OFFICE
CERTIFICATE OF CORRECTION

PATENT NO. : 6,063,768
DATED : May 16, 2000
INVENTOR(S) : First

It is certified that error appears in the above-identified patent and that said Letters Patent is hereby corrected as shown below:

Title Page:

Under Related U.S. Application Data, please delete Provisional application No. 60/020,400 and add -- Provisional application No. 60/025,408 --

Page 1,
Line 6: please delete application Serial No. 60/020,400 and add -- application Serial No. 60/025,408 --

Signed and Sealed this

Seventh Day of August, 2001

*Attest:*

NICHOLAS P. GODICI
*Attesting Officer*    Acting Director of the United States Patent and Trademark Office